United States Patent [19]

Bucher et al.

[11] 4,250,178

[45] Feb. 10, 1981

[54] AMIDES DERIVED FROM CARBOXYL-5 PYRIMIDINES

[75] Inventors: Bernard P. Bucher, Marnes la Coquette; Jean-Francois R. Ancher, Rueil Malmaison; Thierry F. Imbert, Noisy le Roi, all of France

[73] Assignee: Delalande S.A., Courbevoie, France

[21] Appl. No.: 11,752

[22] Filed: Feb. 12, 1979

[30] Foreign Application Priority Data

Feb. 21, 1978 [FR] France .................. 78 04921
Jan. 30, 1979 [FR] France .................. 79 02286

[51] Int. Cl.³ ............... A61K 31/505; C07D 239/47; C07D 403/12
[52] U.S. Cl. .................. 424/251; 544/295; 544/319; 544/320; 544/321; 544/311
[58] Field of Search ............ 544/319, 320, 295, 321, 544/311; 424/251

[56] References Cited

U.S. PATENT DOCUMENTS 2,789,979   4/1957   Rorig et al. .................. 544/320

Primary Examiner—Paul M. Coughlan, Jr.
Attorney, Agent, or Firm—Blanchard, Flynn, Thiel, Boutell & Tanis

[57] ABSTRACT

Compounds for the formula

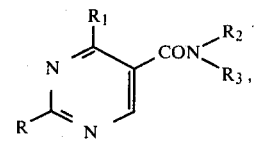

for example,

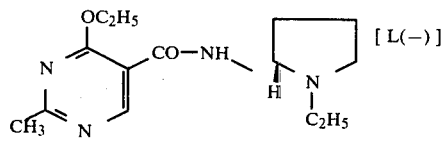

are prepared by reacting

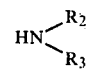

with

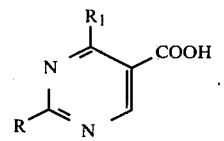

The compounds possess neuroleptic properties.

12 Claims, No Drawings

AMIDES DERIVED FROM CARBOXYL-5 PYRIMIDINES

The present invention relates to novel amides derived from 5-carboxyl pyrimidines, the preparation and the therapeutical application thereof.

The new derivatives of the invention correspond more exactly to the general formula:

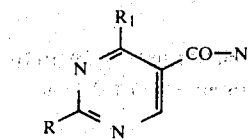

in which the group

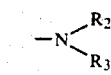

represents:
the aziridine group:

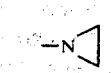

in which case the couple (R, $R_1$) assumes the value ($NH_2$, $OCH_3$);
the chain:

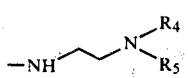

in which the group

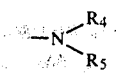

represents:
the 1,2,3,4-tetrahydroisoquinoline group, in which case the couple (R, $R_1$) assumes the value ($NH_2$, $OCH_3$);
a diethylamino group, in which case the couple (R, $R_1$) assumes anyone of the following values: ($NH_2$, $OCH_3$), ($NH_2$, OEt), ($CH_3$, $OCH_3$), ($CH_3S$, $OCH_3$),

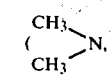

$OCH_3$);
an anilino group, in which case the couple (R, $R_1$) assumes the value ($NH_2$, $OCH_3$);
a benzylamino group

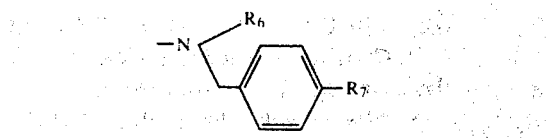

in which the couple ($R_6$, $R_7$)
assumes the value ($CH_3$, H), in which case the couple (R, $R_1$) assumes the value ($NH_2$, $OCH_3$);
assumes the value (Et, H), in which case the couple (R, $R_1$) assumes anyone of the following values ($NH_2$, $OCH_3$), ($CH_3$, $OCH_3$), ($CH_3$, OEt); or
assumes the value (Et, F), in which case the couple (R, $R_1$) assumes the value ($CH_3$, $OCH_3$) or ($CH_3$, OEt);
an N-ethyl N-cyclohexylmethyl amino group of formula

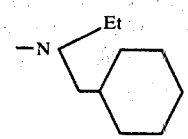

in which case the couple (R, $R_1$) assumes the value ($CH_3$, $OCH_3$); or
an 4-aryl piperazino group of formula:

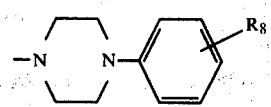

in which $R_8$ represents:
either a hydrogen atom or a fluorine atom in the para position, in which cases the couple (R, $R_1$) assumes the value ($CH_3$, $OCH_3$),
or a methoxy group in the ortho position, in which case the couple (R, $R_1$) assumes the values ($NH_2$, $OCH_3$) and ($CH_3$, $OCH_3$);
the chain

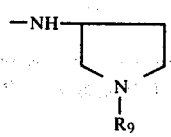

in which $R_9$ represents:
a cyclohexyl group, in which case the couple (R, $R_1$) assumes the value ($NH_2$, $OCH_3$); or
a benzyl or para fluorobenzyl group, in which cases the couple (R, $R_1$) assumes the values ($NH_2$, $OCH_3$) and ($CH_3$, $OCH_3$);
the chain

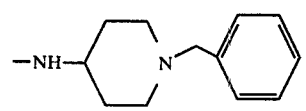

in which case the couple (R, $R_1$) assumes anyone of the following values: ($NH_2$, $OCH_3$), ($CH_3$, $OCH_3$), (H, $OCH_3$), ($CH_3O$, $OCH_3$), (

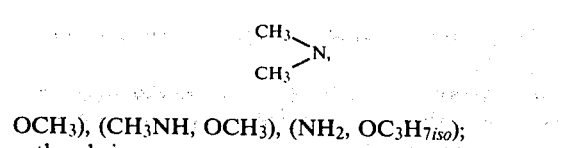

$OCH_3$), ($CH_3NH$, $OCH_3$), ($NH_2$, $OC_3H_{7iso}$);
the chain

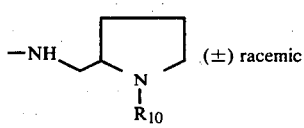 (±) racemic in which $R_{10}$ represents:
  a methyl group, in which case the couple $(R, R_1)$ assumes anyone of the following values: $(NH_2, OCH_3)$, $(CH_3, OCH_3)$, $(CH_3, OEt)$, $(Et, OEt)$;
  an ethyl group, in which case the couple $(R, R_1)$ assumes anyone of the following values: $(NH_2, OCH_3)$, $(NH_2, OEt)$, $(NH_2, OC_3H_{7n})$, $(NH_2, OC_3H_{7iso})$, $(CH_3$-$NH, OCH_3)$, (

$OCH_3$), $(H, OCH_3)$, $(CH_3, OCH_3)$, $(CH_3, OEt)$, $(CH_3, OC_3H_{7n})$, $(CH_3, OC_3H_{7iso})$, $(Et, OEt)$, $(C_3H_{7n}, OCH_3)$, $(C_3H_{7iso}, OCH_3)$, $(CH_3O, OCH_3)$, $(CH_3S, OCH_3)$;
  an n-propyle, n-butyl, benzyl or para-fluorobenzyl group, in which cases the couple $(R, R_1)$ assumes the values: $(NH_2, OCH_3)$ and $(CH_3, OCH_3)$; or
  a cyclohexylmethyl or allyl group, in which cases the couple $(R, R_1)$ assumes the value $(CH_3, OCH_3)$;
  the chain

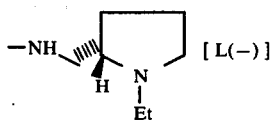 [L(–)]

in which case the couple $(R, R_1)$ assumes anyone of the following values: $(CH_3, OCH_3)$, $(CH_3, OEt)$,

$OCH_3$),

$OEt$); or
  the chain

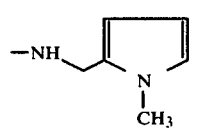, in which case the couple $(R, R_1)$ assumes the value $(CH_3, OCH_3)$.

The compounds of formula (I) of the invention are obtained by using a process which consists in condensing the amines of formula

in which

has the same meanings as in formula (I), with the corresponding 5-carboxyl pyrimidines of formula:

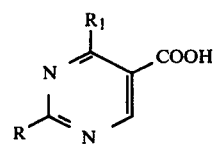 (II)

in which the couple $(R, R_1)$ has the same meanings as in formula (I).

This condensation is carried out preferably by the method of the mixed anhydrides, in an organic solvent, e.g. dimethyl formamide at a temperature of 0° C.

The compounds of formula (II), except for those where the couple $(R, R_1)$ assumes the values $(CH_3O, OCH_3)$ and $(CH_3S, OCH_3)$ are new. They are obtained by saponification of the compounds of formula:

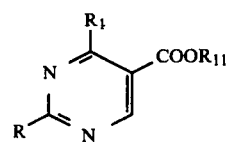 (III)

in which $R_{11}$ represents a methyl, ethyl or n-propyl group and the couple $(R, R_1)$ has the same meaning as in formula (II) except for the values $(CH_3O,OCH_3)$ and $(CH_3S, OCH_3)$.

The compounds of formula (III) for which the set $(R, R_1, R_{11})$ assumes the following values: $(NH_2, OCH_3, CH_3)$, $(NH_2, OEt, Et)$, $(NH_2, OC_3H_{7n}, Et)$, $(NH_2, OC_3H_{7iso}, Et)$, $(CH_3, OEt, Et)$, $(CH_3, OC_3H_{7n}, C_3H_{7n})$, $(CH_3NH, OCH_3, CH_3)$,

$OCH_3, CH_3$),

$OEt, Et)$, $(Et, OEt, Et)$, $(C_3H_{7n}, OCH_3, CH_3)$ and $(C_3H_{7iso}, OCH_3, CH_3)$ are new and those for which R represents the amino group are obtained by a three stage synthesis, which consists in treating the compounds of formula:

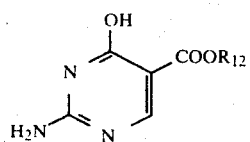
(IV)

where $R_{12}$ represents a methyl or ethyl group, preferably in solution in a basic organic solvent, such as pyridine, by an acid anhydride, e.g. acetic anhydride, then in reacting the new product thus obtained with a chlorinating agent, preferably phosphorous oxychloride, and finally in reacting on the raw product obtained an alcoholate of formula:

$R_1M$ (V)

in which $R_1$ represents a methoxy, ethoxy, n-propoxy or isopropoxy group and M an alkali metal, e.g. sodium.

The novel compounds of formula (III) for which R has the same meanings as in formula (I) except for the hydrogen atom and the amino, methoxy or methylthio group, are obtained by action of methanol or of an alcoholate of formula:

$R'_1$-M (V')

where $R'_1$ represents a methoxy, ethoxy or n-propoxy group, on the chlorinated derivatives of formula:

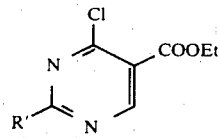
(VI)

in which R' has the same meaning as R in formula (I) with the exception of the hydrogen atom and the amino, methoxy or methylthio group.

The compounds of formula (VI) for which R' represents the following groups: N-methylamino, N,N-dimethylamino, ethyl, n-propyl and isopropyl, are new. They are obtained by the action of phosphorous oxychloride on the compound of formula:

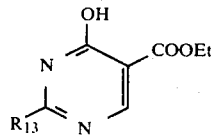
(VII)

in which $R_{13}$ represents an N-methylamino, N,N-dimethylamino, ethyl, n-propyl or iso propyl group.

The compounds of formula (VII) in which the group $R_{15}$ represents an ethyl, n-propyl or isopropyl group are new and are prepared by cyclization, preferably in an alcohol medium and in the presence of sodium ethylate, of the hydrochloride of the amidine of formula:

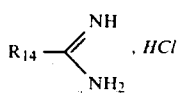
(VIII)

in which $R_{14}$ represents an ethyl, n-propyl or isopropyl group, with ethyl ethoxy methylene malonate.

The derivatives of formula (I) in which R represents an amino group may also be obtained by using a process which consists in condensing the chlorides of the -5 carboxyl pyrimidines of formula:

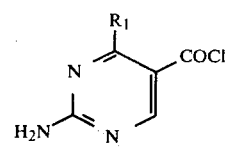
(IX)

in which $R_1$ has the same significance as in formula (I), with the corresponding amines of formula

where the group

has the same significance as the group

in formula (I), except for the following values:

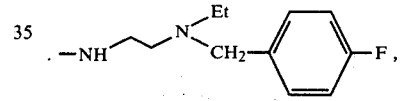

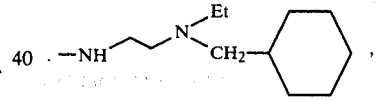

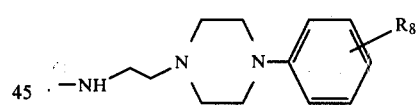

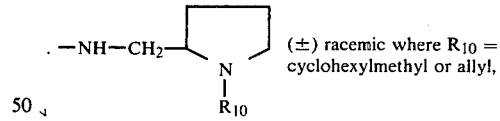

 (±) racemic where $R_{10}$ = cyclohexylmethyl or allyl,

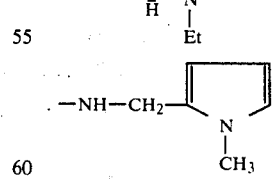 [L(−)],

The condensation is effected preferably in a tetrahydrofuran medium in the presence of triethylamine at a temperature of approximately 0° C.

The novel compounds of formula (IX) are obtained by the action of a chlorinating agent, e.g. phosphorous pentachloride in ethyl ether, on compounds of formula (II) in which R represents an amino group.

The derivatives of formula (I) in which the couple (R, $R_1$) assumes the value ($NH_2$, $OCH_3$) and the group $$-N\begin{matrix}R_2\\R_3\end{matrix}$$

represents the chain $$-NH\underset{}{\diagdown}N\begin{matrix}R'_4\\R'_5\end{matrix}$$

in which the group $$-N\begin{matrix}R'_4\\R'_5\end{matrix}$$

has the same significance as the group $$-N\begin{matrix}R_4\\R_5\end{matrix}$$

in formula (I), except for the following values:

$-N\begin{matrix}Et\\CH_2-\end{matrix}$—⟨phenyl⟩—F, $-N\begin{matrix}Et\\CH_2-\end{matrix}$—⟨cyclohexyl⟩, $-N$⟨piperazine⟩$N$—⟨phenyl⟩—$R_8$   where $R_8 = H$, 4-F, can further be obtained by reaction of the compound of formula:

(X)

[structure with $OCH_3$, $H_2N$, N, O ring]

with the amines of formula $$H-N\begin{matrix}R'_4\\R'_5\end{matrix}$$

in which the group $$-N\begin{matrix}R'_4\\R'_5\end{matrix}$$

has the same significance as above. This reaction is effected preferably in dimethylformamide, in the presence of hydrochloric acid and at a temperature of about 50° C.

The new compound of formula (X) is obtained by condensation of 2-amino bromethane on the compound of formula (II) in which the couple (R, $R_1$) assumes the value ($NH_2$, $OCH_3$), preferably according to the mixed anhydrides method. The raw condensation product is then treated with an organic base, e.g. triethylamine, preferably with reflux in an organic solvent, e.g. ethanol.

The following preparations are given by way of example to illustrate the invention.

EXAMPLE 1:

4-ethoxy 2-ethyl 5-(1-methyl pyrrolidin-2-yl)methylamino carbonyl pyrimidine, fumarate (I) Code number 781021

Stage 1: 5-ethoxycarbonyl 4-hydroxy 2-ethyl pyrimidine (VII) Code number: 780557

To a solution of 35.5 g of sodium in 3 l of ethanol brought to 30° C. there was added 167 g of propionamidine hydrochloride (VIII). The solution was then stirred at 40° C. for 2 hours and the sodium chloride formed was filtered. To the filtrate cooled to 0° C. by an ice bath there was slowly added 350 ml of ethyl ethoxymethylene malonate. This was stirred for 12 hours and then heated to 40° C. for 2 hours. A part of the solvent (approx. 2.5. l) was evaporated, the remainder was iced, the precipitate formed was filtered, washed with ether and recrystallized from ethyl acetate. 113.5 g of the expected product was thus isolated.

Yield: 38%
Melting point: 170° C.
Empirical formula: $C_9H_{12}N_2O_3$
Elementary analysis:

|  | C | H | N |
|---|---|---|---|
| Calculated % | 55.09 | 6.16 | 14.28 |
| Obtained % | 54.80 | 6.29 | 14.57 |

By the same process, but from the corresponding reagents, the compounds of formula (VII) below were obtained.

| Code number | $R_{12}$ | Empirical formula | Melting point (°C.) | Yield (%) | ELEMENTARY ANALYSIS % | C | H | N |
|---|---|---|---|---|---|---|---|---|
| 780704 | $C_3H_{7n}$ | $C_{10}H_{14}N_2O_3$ | 131 | 41 | Cal. | 57.13 | 6.71 | 13.33 |
|  |  |  |  |  | Obt | 57.14 | 6.88 | 13.33 |
| 780911 | $C_3H_{7iso}$ | " | 143 | 25 | Cal. | 57.13 | 6.71 | 13.33 |
|  |  |  |  |  | Obt. | 56.87 | 6.79 | 13.40 |

Stage 2: 5-ethoxycarbonyl 4-chloro 2-ethyl pyrimidine (VI) Code number: 780556

7.5 ml of triethylamine were slowly introduced into 300 ml of phosphorous oxychloride cooled to 0° C., then were added 30 g of 5-ethoxycarbonyl 4-hydroxy 2-ethyl pyrimidine (VII) prepared in the preceding stage and the suspension was brought up to 40° C. under nitrogen scavenging. After dissolution, the phosphorous oxychloride was evaporated and the residue diluted in a mixture of water and chloroform. This was decanted, the chloroform phase was twice washed with water, dried on sodium sulfate and the solvent evaporated. The raw product obtained, after checking the purity by thin layer chromatography, was reacted in the following stage 3.

By the same process, but from the corresponding reagents, the following compounds of formula (VI) were obtained:

5-ethoxycarbonyl 4-chloro 2-methylamino pyrimidine [Code No: 771223, melting point: 70° C.];
2-N,N-dimethylamino 4-chloro 5-ethoxycarbonyl pyrimidine [Code No: 771072, oil];
5-ethoxycarbonyl 4-chloro 2-n-propyl pyrimidine [Code No: 780703, oil];
5-ethoxycarbonyl 4-chloro 2-isopropyl pyrimidine [Code No.: 780910, oil].

These compounds were used in the new state (after checking by thin layer chromatography) for the synthesis of the corresponding compounds of formula (III) described in the next stage.

Stage 3: 5-ethoxycarbonyl 4-ethoxy 2-ethyl pyrimidine (III) Code number: 781019

To a solution cooled to 0° C. of 64.5 g of 5-ethoxycarbonyl 4-chloro 2-ethyl pyrimidine obtained in the preceding stage, in 200 ml of ethanol, was slowly added a solution of 7.75 g of sodium in 200 ml of ethanol, this being stirred for 15 min. after the addition. Then the solution was acidified to a pH≃3 with hydrochloric ethanol≃6.5 N, and the solvent was evaporated. The residue was diluted in water, extracted with chloroform, dried on sodium sulfate and the solvent evaporated. The residue was distilled and 46.7 g of the expected product were obtained.

Yield: 68%
Boiling point (1 mm Hg): 102°–110° C.

| NMR Spectrum (CDCl$_3$) : ppm | = 9.2, s, H in 6 (pyrimidinic) |
|---|---|
| | = 4.56, q, and 4.38, q, (J = 7 Hz) 2 groups —CH$_2$— of —O—CH$_2$—CH$_3$ in 4 and of —COO—CH$_2$—CH$_3$ in 5 |
| | = 2.90, q, (J = 7 Hz), —CH$_2$— of the group —CH$_2$—CH$_3$ in 2 |
| | = 2.25, (t); 2.19, (t); 2.15 (t); 2.15 (t), (J = 7 Hz) 3 groups —CH$_3$ |

IR Spectrum: ester bands at 1730–1700 cm$^{-1}$.

By the same process, but from the corresponding reagents, the compounds of formula (III) appearing in table A below were obtained.

Stage 4: 5-(4-ethoxy 2-ethyl pyrimidinyl) carboxylic acid (II) Code number: 781020

A suspension of 46.2 g of 5-ethoxycarbonyl 4-ethoxy 2-ethyl pyrimidine, obtained in the preceding stage, in a solution of 9.2 g of NaOH in 150 ml of water were stirred at room temperature for 45 mins. Then it was acidified to a pH≃3 by means of concentrated hydrochloric acid and extracted with chloroform. It was dried on sodium sulfate and the solvent was evaporated. The residue was crystallized in hexane and recrystallized from ethyl acetate. Thus 29.3 g of the expected product were obtained.

Yield: 72%
Melting point: 123° C.
Empirical formula: C$_9$H$_{12}$N$_2$O$_3$
Molecular weight: 196.20
Elementary analysis:

|  | C | H | N |
|---|---|---|---|
| Calculated % | 55.09 | 6.17 | 14.28 |
| Obtained % | 55.25 | 6.22 | 14.49 |

By the same process, but from the corresponding reagents, there were obtained the compounds of formula (II) appearing in table B below and having code numbers: 770768–780854–780431–790022–770688–771225–771074–781173–780701–780908.

Stage 5: 4-ethoxy 2-ethyl 5-(1-methyl pyrrolidin-2-yl)methylaminocarbonyl pyrimidine, fumarate (I) Code number: 781021

To a solution of 6.9 g of 5-(4-ethoxy 2-ethyl pyrimidinyl) carboxylic acid prepared in the preceding stage, in 100 ml of tetrahydrofuran, there was added 4.95 ml of triethylamine, then it was cooled to a temperature between 0° and 5° C. and 3.35 ml of ethyl chloroformate were added. It was stirred for 20 min. then 4 g of 2-aminoethyl 1-methyl pyrrolidine were added. After 12 hours at room temperature, the solvent was evaporated, the residue was taken up in chloroform, washed with a solution of NaOH≃2 N, in water, with a dilute hydrochloric acid solution ≃1 N, and finally with water, dried on sodium sulfate and the solvent was evaporated. The residue was filtered on an alumine column and eluted with chloroform. 9.9 g of oil were obtained which has dissolved in a suspension of 5.7 g of fumaric acid in 100 ml of acetone. Then the precipitate obtained was filtered and recrystallized from ethanol. Thus 10.1 g of the desired product were isolated.

Yield: 76%
Melting point: 150° C.

Empirical formula: C$_{15}$H$_{24}$N$_4$O$_2$, C$_4$H$_4$O$_4$
Molecular weight: 408.45
Elementary analysis:

|  | C | H | N |
|---|---|---|---|
| Calculated % | 55.87 | 6.91 | 13.72 |
| Obtained % | 56.04 | 7.14 | 14.01 |

By the same process, but from the corresponding reagents, there were obtained the compounds of formula (I) appearing in table C below.

EXAMPLE 2

1-[5-(2-amino 4-methoxy pyrimidinyl) carboxamido] 2-[N-methyl N-benzylamino] ethane (I) Code number: 770512

Stage 1: 2-amino 4-methoxy 5-methoxycarbonyl pyrimidine (III) Code number: 760286

50 g of 2-amino 4-hydroxy 5-ethoxy carbonyl pyrimidine were brought to reflux with 40 ml of acetic anhydride in 300 ml of anhydrous pyridine for 2 hours. The reaction medium was then frozen, the precipitate separated by filtration, rinsed with acetone and dried. 140 g of raw product thus obtained (yield 62%) were brought up to 60° C. in 900 ml of phosphorous oxychloride for two hours. After cooling, 200 ml of ethyl ether were added while stirring; the precipitate formed was then separated by filtration rinsed with ether, then thrown on 1 kg of ice, neutralized with a solution of sodium bicarbonate while stirring. The precipitate was separated by filtration, rinsed with water and dried. 112 g of this intermediate product (yield 81%) were stirred for 2 hours in a solution of sodium methanolate at 0° C., prepared with 46 g of sodium in 800 ml of anhydrous methanol. After coming back to normal temperature, the precipitate was separated by filtration, rinsed with water and dried. 80 g of 2-amino 4-methoxy 5-methoxycarbonyl pyrimidine were obtained.

Yield: 95%

Melting point 221° C. after recrystallization from BuOH

Empirical formula of the hydrochloride: $C_7H_{10}ClN_3O_3$

Molecular weight of the hydrochloride: 219.631

Melting point of the hydrochloride: 260° C.

Elementary analysis:

|  | C | H | N |
|---|---|---|---|
| Calculated % | 38.28 | 4.59 | 19.13 |
| Obtained % | 38.28 | 4.42 | 19.39 |

With the same operating method, but from the corresponding reagents, the following compounds were obtained: 2-amino 4-ethoxy 5-carbonyl pyrimidine Code number: 770505

Empirical formula: $C_9H_{13}N_3O_3$

Molecular weight: 211.218

Melting point: 190° C. after recrystallization in BuOH

NMR Spectrum (DMSO) δppm 2 triplets centered at 1.3 ppm 6H (OCH$_2$CH$_3$) 2 quadruplets centred at 4.3 ppm 4H (OCH$_2$—CH$_3$) 1 multiplet centred at 7.2 ppm 2H (NH$_2$) 1 singleton centred at 8.5 ppm 1H Ar-H IR Spectrum: (KBr) γcm$^{-1}$ 3370 cm$^{-1}$ (NH$_2$): 1680 cm$^{-1}$ (ester)

2-amino 4-n-propoxy ethoxy 5-carbonyl pyrimidine Code number: 770640

2-amino 4-i-propoxy 5-ethoxy carbonyl pyrimidine Code number: 770867

These last two compounds were used in the raw state in the further step after checking their purity by thin layer chromatography.

Stage 2: 5-(2-amino 4-methoxy pyrimidinyl) carboxylic acid (II) Code number: 760 795

600 g of 2-amino 4-methoxy 5-methoxycarbonyl pyrimidine were brought to 65° C. while stirring for 1 hour in a mixture of 1.5 l of methanol and 1.5 l of 5% NaOH. Once cooled, the reaction medium was poured on to 4 l of frozen water then acidified while stirring with concentrated hydrochloric acid to pH 3. The 5-(2-amino 4-methoxy pyrimidinyl) carboxylic acid precipitated had the water removed, was washed with acetone then dried.

Yield: 88.5%

Empirical formula of the hydrated sodium salt: $C_6H_6N_3O_3Na$, 1.25 H$_2$O

Molecular weight of the hydrated sodium salt: 213.810

Melting point of the hydrated sodium salt: 260° C.

Elementary analysis:

|  | C | H | N |
|---|---|---|---|
| Calculated % | 33.73 | 4.01 | 19.67 |
| Obtained % | 34.05 | 3.73 | 19.84 |

By the same process, but from the corresponding reagents, the compounds of formula (II) having code numbers 770506, 770641 and 770868, shown in table B below, were obtained.

Stage 3: 2-amino 4-methoxy 5-chlorocarbonyl pyrimidine hydrochloride (IX) Code number: 770475

To 16.9 g of 2-amino 4-methoxy 5-pyrimidinyl carboxylic acid prepared in stage 2, in suspension in 300 ml of anhydrous ethyl ether, were added at 0° C., 20.8 g of phosphorous pentachloride while stirring. After returning to room temperature for 3 hours, the precipitate was separated by filtration, rinsed several times with 50 ml of absolute ethyl ether. The hydrochloride of the 2-amino 4-methoxy 5-chlorocarbonyl pyrimidine thus obtained was used in the raw state in the following stage.

With the same operation method, but from the corresponding reagents, the following compounds were obtained:

2-amino 4-ethoxy 5-chlorocarbonyl pyrimidine hydrochloride Code number: 770507; IR Spectrum γcm$^{-1}$ 1770 (acid chloride)

2-amino 4-n-propoxy 5-chlorocarbonyl pyrimidine hydrochloride Code number: 770642

2-amino 4-iso-propoxy 5-chlorocarbonyl pyrimidine Code number: 770869

These compounds were used in the raw state in the next stage.

Stage 4: 1-[5-(2-amino 4-methoxy pyrimidinyl) carboxamido] 2-[N-methyl N-benzylamino] ethane (I) Code number 770512

To a solution of 12.4 g of triethylamine and 8.1 g of 2-N-methyl N-benzylamino ethylamine in 200 ml of tetrahydrofuran was added at 0° C. while stirring the 5-(2-amino 4-metoxy chlorocarbonyl) pyrimidine hydrochloride obtained in the third stage. After stirring for 3 hours, with return to normal temperature, the tetrahydrofuran was vacuum evaporated and the residue taken up in 100 ml of carbonated water to pH 9. Separated by filtration and rinsed with distilled water, the precipitate was dried and recrystallized from absolute ethanol to give 5.5 g of 1-[5-(2-amino 4-methoxy pyrimidinyl)carboxamido] 2-[N-methyl N-benzylamino] ethane.

Yield: 36%

Empirical formula: $C_{16}H_{21}N_5O_2$

Molecular weight: 315.368
Melting point: 192° C.
Elementary analysis:

|  | C | H | N |
|---|---|---|---|
| Calculated % | 60.93 | 6.71 | 22.21 |
| Obtained % | 60.63 | 6.59 | 22.40 |

The derivatives of formula (I) in which R=NH$_2$ and appearing in table C, were also synthesized by an operating method identical to that of example 2.

EXAMPLE 3:

1-[5-(2-amino 4-methoxy pyrimidinyl) carboxamido] 2-[(tetrahydro 1,2,3,4) isoquinolin-2-yl] ethane (I) Code number: 770862

Stage 1: 2-amino 4-methoxy 5-(1,3-oxazolin-2-yl) pyrimidine Code number: 770861

To a suspension of 34 g of 5-(2-amino 4-methoxy pyrimidinyl)carboxylic acid, prepared in the second stage of example 2, in 500 ml of dimethyl formamide in the presence of 50 ml of triethylamine, were added drop by drop, at 0° C., while stirring, 14 ml of ethyl chloroformiate; the stirring was maintained for 1 hour at this temperature and 41.6 g of 2-amino bromoethane hydrobromide were introduced. After 20 hours stirring at room temperature, the reaction medium was vacuum concentrated, then taken up at reflux with 200 ml of ethanol and 20 ml of triethylamine, for 3 hours. After evaporation of the ethanol, the residue was taken up in carbonated water for 1 hour with stirring. The 2-amino 4-methoxy 5-(1,3-oxazolin-2-yl) pyrimidine precipitated was separated by filtration and rinced with acetone.
Yield: 26%
Melting point 226° C.
Empirical formula of the monomaleate: C$_{12}$H$_{14}$N$_4$O$_6$ Molecular weight of the monomaleate: 310.264
Melting point of the monomaleate: 188° C.
Elementary analysis of the monomaleate:

|  | C | H | N |
|---|---|---|---|
| Calculated % | 46.45 | 4.55 | 18.06 |
| Obtained % | 46.25 | 4.52 | 17.86 |

Stage 2: 1-[5-(2-amino 4-methoxy pyrimidinyl) carboxamido] 2-[(tetrahydro-1,2,3,4)isoquinolin-2-yl)]ethane Code number: 770862

8 g of 2-amino 4-methoxy 5-(1,3-oxazolin-2-yl) pyrimidine obtained in the preceding stage, were brought to 110° C., for three hours, with stirring, with 6.65 g of tetrahydro-1,2,3,4 isoquinoline and 2 ml of concentrated hydrochloric acid in 300 ml of dimethyl formamide. After evaporation of the solvent, the reaction medium was taken up in 70 ml of carbonated water while stirring, the precipitate formed was separated by filtration and rinsed with acetone then with ethyl ether. Dried, the 1-[5-(2-amino 4-methoxy pyrimidinyl) carboxamido] 2-[(tetrahydro-1,2,3,4) isoquinolin-2-yl)] ethane was obtained with a yield of 54%. The monomaleate was obtained by adding a maleic acid equivalent to the acetone suspension of the basic derivative; it was recrystallized in 96 ethanol.
Empirical formula: C$_{21}$H$_{25}$N$_5$O$_6$
Molecular weight: 443.45
Melting point: 200° C.
Elementary analysis:

|  | C | H | N |
|---|---|---|---|
| Calculated % | 56.87 | 5.68 | 15.79 |
| Obtained % | 56.48 | 5.48 | 15.74 |

TABLE A

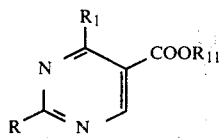

(III)

| Code number | R | R$_1$ | R$_{11}$ | Empirical formula | Molecular weight | Melting or boiling point (°C.) | Yield (%) | Elementary analysis, NMR spectrum or IR spectrum | | | |
|---|---|---|---|---|---|---|---|---|---|---|---|
|  |  |  |  |  |  |  |  | % | C | H | N |
| 780853 | CH$_3$ | OEt | Et | C$_{10}$H$_{14}$N$_2$O$_3$ | 210.23 | (raw) M.P.<50° C. | 63 |  |  |  |  |
| 780430 | CH$_3$ | OC$_3$H$_7$ n | C$_3$H$_7$ n | C$_{12}$H$_{18}$N$_2$O$_3$ | 238.28 | B.P. (0.8) = 120° C. | 71 | Calc. Obt. | 60.48 60.24 | 7.61 7.52 | 11.76 12.06 |
| 771224 | CH$_3$NH | OCH$_3$ | CH$_3$ | C$_8$H$_{11}$N$_3$O$_3$ | 197.19 | M.P. = 145° C. | 43 | NMR spectrum (CF$_3$COOH)δppm = 8.83, s, H (pyrimidinic) in 6 4.23, s, and 4.04, s, 2 OCH$_3$ 3.42, d, —N(CH$_3$)(H) IR spectrum: band COOCH$_3$ to 1739 cm$^{-1}$ | | | |
| 781172 | 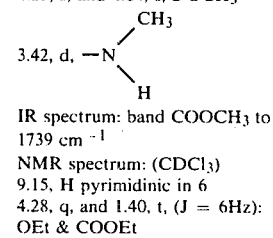 | OEt | Et | C$_{11}$H$_{17}$N$_3$O$_3$ | 239.27 | (raw) M.P. = 350° C. | 59 | NMR spectrum: (CDCl$_3$) 9.15, H pyrimidinic in 6 4.28, q, and 1.40, t, (J = 6Hz): OEt & COOEt | | | |

TABLE A-continued (III)

Structure: pyrimidine with R at 2-position, R₁ at 4-position, COOR₁₁ at 5-position

| Code number | R | R₁ | R₁₁ | Empirical formula | Molecular weight | Melting or boiling point (°C.) | Yield (%) | Elementary analysis, NMR spectrum or IR spectrum |
|---|---|---|---|---|---|---|---|---|
| 780702 | $C_3H_7$ n | $OCH_3$ | $CH_3$ | $C_{10}H_{14}N_2O_3$ | 210.23 | B.P. (1) = 98°–108° C. | 73 | NMR spectrum (CDCl₃) δppm = 9.00, s, H pyrimidinic in 6; 4.1, s, and 3.9, s, OCH₃ and COOCH₃; 2.8, t, (J = 7Hz) 1.9, m, (J = 7Hz) 1.00(t) J = 7Hz ($C_3H_7$n); IR spectrum COOCH₃ to 1735 cm⁻¹ |
| 780909 | $C_3H_7$ iso | $OCH_3$ | $CH_3$ | $C_{10}H_{14}N_2O_3$ | 210.23 | B.P. (0.1) = 80°–95° C. | 76 | NMR spectrum (CDCl₃) δppm = 9.1, s, H pyrimidinic; 4.1, s, and 3.9, s, OCH₃ and COOCH₃; 3.1, m and 1,3, d: —CH(CH₃)₂; IR spectrum: band COOCH₃ to 1730 cm⁻¹ |
| 771073 | (CH₃)₂N— | $OCH_3$ | $CH_3$ | $C_9H_{13}N_3O_3$ | 211.22 | 126 | 48 | NMR spectrum (CF₃COOH), δppm = 4 and 4.2, s, 2 OCH₃; 3.4, d, —N(CH₃)₂; 8.9, s, H pyrimidinic in 6; IR: band COOCH₃ to 1730 cm⁻¹ |

TABLE B (II)

Structure: pyrimidine with R at 2-position, R₁ at 4-position, COOH at 5-position

| Code number | R | R₁ | Empirical formula | Molecular weight | Melting point (°C.) | Yield (%) | Elementary analysis, NMR spectrum or IR spectrum |
|---|---|---|---|---|---|---|---|
| 780854 | $CH_3$ | OEt | $C_8H_{10}N_2O_3$ | 182.18 | 150 | 59 | Calc. C 52.74 H 5.53 N 15.38; Obt. C 52.73 H 5.38 N 15.50 |
| 780431 | $CH_3$ | $OC_3H_7$ n | $C_9H_{12}N_2O_3$ | 196.02 | 138 | 62 | NMR spectrum (CDCl₃) δppm = 13.8, s, : —COOH; 9.30, s, H pyrimidinic in 6; 4.51, t, (J = 7Hz), 1.91, m, (J = 7 Hz) and 1.04, t, (J = 7Hz), OC₃H₇; 2.68, s, CH₃ |
| 790022 | $CH_3$ | O—$C_3H_7$ iso | $C_9H_{12}N_2O_3$ | 196.02 | 185 | 75 | |
| 771225 | $CH_3NH$ | $OCH_3$ | $C_7H_9N_3O_3$ | 166.00 | 158 | 80 | |
| 781173 | (CH₃)₂N— | OEt | $C_9H_{13}N_3O_3$ | 211.22 | 211 | 65 | calc. C 51.71 H 6.20 N 19.90; Obt. C 51.07 H 6.26 N 19.76 |
| 780701 | $C_3H_7$ n | $OCH_3$ | $C_9H_{12}N_2O_3$ | 196.20 | 144 | 60 | calc. C 55.09 H 6.17 N 14.28; Obt. C 55.16 H 5.87 N 14.29 |
| 780908 | $C_3H_7$ iso | $OCH_3$ | $C_9H_{12}N_2O_3$ | 196.20 | 110 | 73 | calc. C 55.09 H 6.17 N 14.28; Obt. C 55.07 H 6.23 N 14.46 |
| 770768 | $CH_3$ | $OCH_3$ | $C_7H_8N_2O_3$ | 168.15 | 189 | 78 | NMR spectrum (DMSO) δppm = 2.6, s, CH₃; 4.00, s, OCH₃; 8.70, s, H pyrimidinic in 6 |

TABLE B-continued

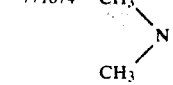
(II)

| Code number | R | $R_1$ | Empirical formula | Molecular weight | Melting point (°C.) | Yield (%) | Elementary analysis, NMR spectrum or IR spectrum | | | |
|---|---|---|---|---|---|---|---|---|---|---|
| | | | | | | | % | C | H | N |
| 770668 | H | $OCH_3$ | $C_6H_6N_2O_3$ | 154.12 | 210 | 71 | NMR spectrum (DMSO) δppm = 4.00, s, $OCH_3$ 8.90, s, 2 H pyrimidinic in 2 & 6 | | | |
| 771074 | $CH_3\!\!-\!\!N\!\!-\!\!CH_3$ | $OCH_3$ | $C_8H_{11}N_3O_3$ | 197.19 | 215 | 67 | calc. Obt. | 48.72 48.86 | 5.62 5.69 | 21.31 21.20 |
| 770506 | $NH_2$ | OEt | $C_7H_9N_3O_3$ | 183.16 | 280 | 72 | NMR spectrum ($CF_3COOH$) δppm = 8.80, s, 1 H pyrimidinic 7.50, m, $-NH_2$ in 4 4.75, q, (J ≃ 7Hz) and 1.50, t, (J ≃ 7Hz) $-OCH_2-CH_3$ | | | |
| 770641 | $NH_2$ | $OC_3H_{7n}$ | $C_8H_{11}N_3O_3$ | 197.13 | >260 | 68 | NMR spectrum ($D_2O$) δppm = 8.38, s, 1 H pyrimidinic 4.23, t, (J ≃ 7Hz); 1.72, m, (J ≃ 7Hz) and 0.92, t, (J ≃ 7Hz) $OC_3H_{7n}$ | | | |
| 770868 | $NH_2$ | $OC_3H_{7iso}$ | $C_8H_{11}N_3O_3$ | 197.19 | 270 with decomp. | 75 | | | | |

TABLE C $$\begin{array}{c} R_1 \quad R_2 \\ \diagdown \diagup \\ CON \\ \diagup \quad \diagdown R_3 \\ \text{(heterocycle)} \end{array} \quad (I)$$

| Code number | R | $R_1$ | $-N\begin{smallmatrix}R_2\\R_3\end{smallmatrix}$ | Form | Empirical formula | Molecular weight | Melting point (°C.) | Yield (%) | % | ELEMENTARY ANALYSIS C | H | N |
|---|---|---|---|---|---|---|---|---|---|---|---|---|
| 780327 | $CH_3$ | $OCH_3$ | Et, $CH_2$-phenyl, ethyl-NH | maleate | $C_{22}H_{28}N_4O_6$ | 444.48 | 153 | 33 | Cal. Obt. | 59.45 59.44 | 6.35 6.48 | 12.61 12.75 |
| 780656 | $CH_3$ | OEt | Et, $CH_2$-phenyl, ethyl-NH | diHCl | $C_{19}H_{28}Cl_2N_4O_2$ | 415.46 | 152 | 51 | Cal. Obt. | 54.92 54.66 | 6.79 6.97 | 13.48 13.52 |
| 780886 | $CH_3$ | $OCH_3$ | Et, $CH_2$-(4-F-phenyl), ethyl-NH | 1.6 HCl + ⅔ $H_2O$ | $C_{18}H_{23}FN_4O_2$ + 1.6 HCl + ⅔ $H_2O$ | 416.75 | 158 | 43 | Cal. Obt. | 51.87 52.17 | 6.27 5.90 | 13.44 13.28 |
| 780887 | $CH_3$ | OEt | Et, $CH_2$-(4-F-phenyl), ethyl-NH | 1.3 fumarate | $C_{19}H_{25}FN_4O_2$ + 1.3 $C_4H_4O_4$ | 511.32 | 138 | 25 | Cal. Obt. | 56.84 56.80 | 5.95 5.77 | 10.96 10.91 |
| 78066 | $CH_3$ | $OCH_3$ | Et, $CH_2$-cyclohexyl, ethyl-NH | 2.1 fumarate | $C_{18}H_{30}N_4O_2$ + 2.1 $C_4H_4O_4$ | 508.56 | 140 | 31 | Cal. Obt. | 54.84 54.84 | 6.69 6.76 | 9.69 9.89 |
| 780522 | $CH_3$ | $OCH_3$ | piperazinyl-phenyl, ethyl-NH | base | $C_{19}H_{25}N_5O_2$ | 355.43 | 82 | 68 | Cal. Obt. | 64.20 64.15 | 7.09 6.92 | 19.71 19.71 |
| 780686 | $CH_3$ | $OCH_3$ | piperazinyl-(4-F-phenyl), ethyl-NH | HCl | $C_{19}H_{25}ClFN_5O_2$ | 409.89 | 185 | 56 | Cal. Obt. | 55.67 55.34 | 6.15 6.39 | 17.09 16.77 |

TABLE C-continued $$\text{(I)}$$

| No. | R | $R_1$ | $R_2$, $R_3$ (NR₂R₃) | Salt | Formula | MW | mp | Yield | | C | H | N |
|---|---|---|---|---|---|---|---|---|---|---|---|---|
| 780521 | $CH_3$ | $OCH_3$ | —NH—(piperazine-N-CH₂CH₂-)-C₆H₄-OCH₃ (o) | base | $C_{20}H_{27}N_5O_3$ | 385.46 | 123 | 72 | Cal.<br>Obt. | 62.32<br>62.07 | 7.06<br>6.75 | 18.17<br>17.88 |
| 780326 | $CH_3$ | $OCH_3$ | —NH—(pyrrolidine-N-CH₂-C₆H₅) | 1.9 fumarate + 1/6 H₂O | $C_{18}H_{22}N_4O_2$ + 1.9 $C_4H_4O_4$ + 1/6 H₂O | 550.39 | 200 | 27 | Cal.<br>Obt. | 56.73<br>56.23 | 5.49<br>5.47 | 10.18<br>10.18 |
| 771274 | $NH_2$ | $OCH_3$ | —NH—(pyrrolidine-N-CH₂-C₆H₄-F (p)) | base | $C_{17}H_{20}FN_5O_2$ | 345.37 | 164 | 62 | Cal.<br>Obt. | 59,12<br>59,08 | 5,84<br>5,84 | 20,28<br>20,45 |
| 780560 | $CH_3$ | $OCH_3$ | " | 1.5 fumarate | $C_{24}H_{27}FN_4O_8F$ | 518.49 | 180 | 32 | Cal.<br>Obt. | 55,59<br>55,69 | 5.25<br>5.24 | 10.81<br>11.04 |
| 771261 | $CH_3NH$ | $OCH_3$ | —NH—(piperidine-N-CH₂-C₆H₅) | base | $C_{19}H_{25}N_5O_2$ | 355.43 | 156 | 76 | Cal.<br>Obt. | 64.20<br>63.96 | 7.09<br>7.22 | 19.71<br>19.53 |
| 771226 | $CH_3NH$ | $OCH_3$ | —NH—CH₂-(pyrrolidine-N-Et) (±) | base | $C_{14}H_{23}N_5O_2$ | 293.36 | 130 | 52 | Cal.<br>Obt. | 57.31<br>57,19 | 7.90<br>8.14 | 23.87<br>24.00 |
| 780336 | $CH_3$ | OEt | " | base | $C_{15}H_{24}N_4O_2$ | 292,37 | 54 | 55 | Cal.<br>Obt. | 61.62<br>61.47 | 8.27<br>8.23 | 19.16<br>19.11 |
| 780432 | $CH_3$ | $OC_3H_7$ n | " | base | $C_{16}H_{26}N_4O_2$ | 306,40 | <50 | 37 | Cal.<br>Obt. | 62.72<br>62.47 | 8.55<br>8.90 | 18.29<br>18,01 |
| 780561 | $CH_3$ | O-iPr | " | + 0.54 fumarate | $C_{20}H_{30}N_4O_6$ | 422,47 | 128 | 22 | Cal.<br>Obt. | 59.09<br>59.28 | 7.69<br>7.52 | 15.18<br>15,16 |

TABLE C-continued $$\begin{array}{c} R_1 \quad R_2 \\ \diagdown \diagup \\ CON \\ \diagup \quad \diagdown R_3 \\ \vert \\ N \quad N \\ \diagdown \diagup \\ R \end{array} \quad (I)$$

| | R | R₁ | R₂R₃ | | | | | | | |
|---|---|---|---|---|---|---|---|---|---|---|
| 781022 | Et | OEt | —NH—CH₂—(pyrrolidine N-Et) (±) | 1.5 fumarate | C₂₂H₃₂N₄O₈ | 480,51 | 120 | 31 | Cal. Obt. | 54.99 55.14 | 6.71 6.56 | 11.66 11.72 |
| 780700 | C₃H₇ iso | OCH₃ | " | 1.5 fumarate | C₂₂H₃₂N₄O₈ | 480.51 | 159 | 42 | Cal. Obt. | 54.99 54.90 | 6.71 6.82 | 11.66 11.62 |
| 780907 | C₃H₇ iso | OCH₃ | " | 1.5 fumarate | C₂₂H₃₂N₄O₈ | 480.51 | 179 | 40 | Cal. Obt. | 54.99 54.95 | 6.71 6.54 | 11.66 11.64 |
| 780079 | NH₂ | OCH₃ | —NH—CH₂—(pyrrolidine N-CH₃) (±) | base | C₁₂H₁₉N₅O₂ | 265,31 | 220 | 48 | Cal. Obt. | 54,32 54.16 | 7.21 6.95 | 26.39 26.43 |
| 780680 | CH₃ | OCH₃ | —NH—CH₂—(pyrrolidine N-CH₃) (±) | 1.5 fumarate | C₁₉H₂₆N₄O₈ | 438.43 | 145 | 37 | Cal. Obt. | 52.05 52.07 | 5.98 5.84 | 12.78 12.49 |
| 781017 | CH₃ | OEt | " | fumarate | C₁₈H₂₆N₄O₆ | 394.42 | 159 | 28 | Cal. Obt. | 54.81 55.12 | 6.64 6.71 | 14.21 14.05 |
| 781021 | Et | OEt | " | fumarate | C₁₉H₂₈N₄O₆ | 408.45 | 150 | 76 | Cal. Obt. | 55.87 55.87 | 6.91 6.91 | 13.72 14.01 |
| 771120 | NH₂ | OCH₃ | —NH—CH₂—(pyrrolidine N-C₃H₇n) | base | C₁₄H₂₃N₅O₂ | 293.36 | 189 | 66 | Cal. Obt. | 56.04 57.31 | 7.14 7.90 | 14.01 23.87 |
| 780552 | CH₃ | OCH₃ | —NH—CH₂—(pyrrolidine N-C₃H₇n) | 1.5 fumarate | C₂₁H₃₀N₄O₈ | 466.48 | 156 | 41 | Cal. Obt. | 57.31 57.44 | 7.90 7.89 | 23.87 23.65 |
| 780457 | CH₃ | OCH₃ | —NH—CH₂—(pyrrolidine N-C₄H₉n) | 1.5 fumarate | C₂₂H₃₂N₄O₈ | 480,51 | 142 | 38 | Cal. Obt. | 54.07 54.07 | 6.48 6.24 | 12,01 11.92 |
| | | | | | | | | | Cal. Obt. | 54.98 55.30 | 6.97 6.74 | 11.66 11.67 |

TABLE C-continued $$\begin{array}{c} R_2 \\ | \\ CON-R_3 \\ | \\ R_1 \end{array} \quad (I)$$

| | | | R | | | | | | |
|---|---|---|---|---|---|---|---|---|---|
| 780458 | CH₃ | OCH₃ | —NH—CH₂—(pyrrolidinyl-N-CH₂-phenyl) | 1.5fumarate + 0.9H₂O | C₂₅H₃₀N₄O₈ | 530.74 | 135 | 29 | Cal. 56.57 6.07 10.55<br>Obt. 56.89 6.44 10.79 |
| 780505 | CH₃ | OCH₃ | —NH—CH₂—(pyrrolidinyl-N-CH₂-4-F-phenyl) | 1.5fumarate | C₂₅H₂₉N₄O₈ | 532.51 | 158 | 42 | Cal. 56.38 5.49 10.52<br>Obt. 56.33 5.39 10.77 |
| 780836 | CH₃ | OCH₃ | —NH—CH₂—(pyrrolidinyl-N-CH₂-cyclohexyl) | 1.5fumarate | C₂₅H₃₆N₄O₈ | 520.57 | 131 | 35 | Cal. 57.68 6.97 10,76<br>Obt. 57,53 6.77 10.72 |
| 780784 | CH₃ | OCH₃ | —NH—CH₂—(pyrrolidinyl-N-allyl) | 2.5fumarate | C₂₅H₃₂N₄O₁₂ | 580.54 | 151 | 47 | Cal. 51.72 5.50 9.65<br>Obt. 51,84 5.56 9.56 |
| 780648*1 | CH₃ | OCH₃ | —NH—(pyrrolidinyl-N-Et) (−) | 1.5fumarate | C₂₀H₂₈N₄O₈ | 452.46 | 138 | 58 | Cal. 53.09 6.24 12.38<br>Obt. 52,96 6.26 12.39 |
| 780905*2 | CH₃ | OEt | —NH—(pyrrolidinyl-N-Et) (−) | 1.5fumarate | C₂₁H₃₀N₄O₈ | 466.48 | 112 | 48 | Cal. 54.07 6.48 12.01<br>Obt. 53.78 6.57 12.08 |
| 781171*3 | CH₃ | OCH₃ | —N(CH₃)₂ | base | C₁₅H₂₅N₅O₂ | 307.39 | <50 | 69 | Cal. 58.61 8.20 22.79<br>Obt. 58.18 8.39 23.03 |
| 781170*4 | CH₃ | OEt | —N(CH₃)₂ | base | C₁₆H₂₇N₅O₂ | 321.42 | 59 | 72 | Cal. 59.79 8.47 21.79<br>Obt. 59.09 8.71 21.79 |

TABLE C-continued (I) [structure shown at top right: R₁, R₂, CON-R₃ substituted pyrimidine with R group]

| Code number | R | R₁ | R₂ N R₃ | Empirical formula | Molecular weight | Melting point (°C) | Yield (%) | Calculated % C | H | N | Obtained % C | H | N |
|---|---|---|---|---|---|---|---|---|---|---|---|---|---|
| 780204 | CH₃ | OCH₃ | —NH—CH₂—(N-methylpyrrole) | base C₁₃H₁₆N₄O₂ | 260.29 | | 80 / 75 | 59.98 | 7.92 | 26.20 | 59.91 / 60.08 | 6.20 / 6.09 | 21.53 / 21.62 | x₁[α]_D = −9°64 (C = 1%, H₂O)
x₂[α]_D = −10°8 (C = 5%, H₂O)
x₃[α]_D = 67°6 (C = 1%, CHCl₃)
x₄[α]_D = 67°9 (C = 1%, CHCl₃)

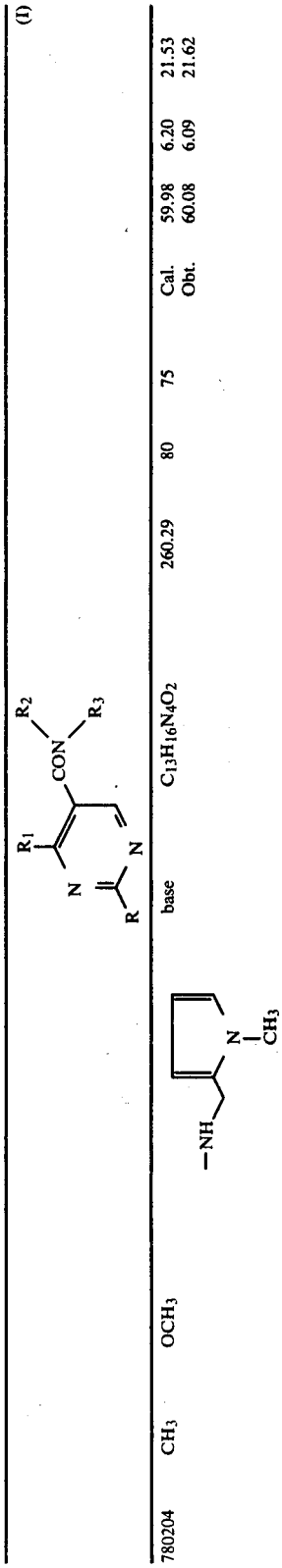

| Code number | R | R₁ | R₂ N R₃ | Empirical formula | Molecular weight | Melting point (°C) | Yield (%) | Calculated % C | H | N | Obtained % C | H | N |
|---|---|---|---|---|---|---|---|---|---|---|---|---|---|
| 76.0745 | NH₂ | OCH₃ | (diethylaminoethyl) | C₁₂H₂₁N₅O₂ | 267.328 | 197 | 68 | 53.91 | 7.92 | 26.20 | 53.74 | 7.99 | 26.00 |
| 76.0843 | " | " | (N-methylpyrrolidinyl-methyl) | C₁₃H₂₁N₅O₂ | 279.338 | 212 | 53 | 55.89 | 7.58 | 25.07 | 55.97 | 7.65 | 25.22 |
| 76.0994 | " | " | (o-methoxyphenyl-piperazinyl-ethyl) | C₁₉H₂₆N₆O₃ | 386.446 | 202 | 40 | 59.05 | 6.78 | 21.75 | 59.19 | 6.81 | 21.82 |
| 77.0489 | " | " | (benzyl-piperazinyl-ethyl) | C₁₇H₂₃N₅O₂ | 329.394 | 158 | 57 | 61.38 | 7.04 | 21.26 | 61.85 | 7.05 | 21.54 |
| 77.0512 | " | " | (N-benzyl-N-methylaminoethyl) | C₁₆H₂₁N₅O₂ | 315.368 | 192 | 36 | 60.93 | 6.71 | 22.21 | 60.63 | 6.59 | 22.40 |
| 77.0958 | " | " | (N-benzyl-pyrrolidinyl) | oxalate C₁₉H₂₃N₅O₆ | 417.414 | 208 | 59 | 54.67 | 5.55 | 16.78 | 54.33 | 5.52 | 16.98 |

TABLE C-continued

| No. | R | R₁ | R₂R₃N- (amine) | Salt / Formula | MW | mp | Yield % | C calc | H calc | N calc | C found | H found | N found |
|---|---|---|---|---|---|---|---|---|---|---|---|---|---|
| 77.1047 | " | " | (S)-2-[(4-fluorobenzyl)aminomethyl]pyrrolidine | maleate C₂₂H₂₆FN₅O₆ | 475.468 | 173 | 48 | 55.57 | 5.51 | 14.73 | 55.87 | 5.72 | 14.90 |
| 77.0766 | CH₃ | " | diethylaminoethylamine | oxalate C₁₅H₂₄N₄O₆ | 356.374 | 170 | 72 | 50.55 | 6.79 | 15.72 | 50.25 | 6.77 | 15.68 |
| 77.0805 | " | " | 2-(aminomethyl)pyrrolidine | ½ H₂O C₁₄H₂₂N₄O₂ | 287.356 | huile | 68 | 58.51 | 8.07 | 19.50 | 58.80 | 8.12 | 19.78 |
| 77.0878 | " | " | 1-benzyl-4-aminopiperidine | maleate C₂₃H₂₈N₄O₆ | 456.486 | 161 | 30 | 60.51 | 6.18 | 12.27 | 60.45 | 6.33 | 12.06 |
| 77.1243 | OCH₃ | OCH₃ | 1-benzyl-2-(aminomethyl)pyrrolidine | 0.8 H₂O C₁₄H₂₂N₄O₃ | 308.700 | — | 76 | 54.4 | 7.65 | 18.15 | 54.82 | 7.56 | 18.42 |
| 77.1244 | " | " | 1-benzyl-4-aminopiperidine | oxalate ⅜ H₂O C₂₁H₂₆N₄O₇ | 458.461 | 130 | 68 | 55.01 | 6,01 | 12.22 | 55.29 | 5.80 | 12.29 |
| 77.0580 | " | " | N-phenylethylenediamine | C₁₄H₁₇N₅O₂ | 287.316 | 210 | 67 | 58.52 | 5.96 | 24.38 | 58.41 | 6.15 | 24.69 |
| 77.0862 | NH₂ | " | 2-(2-aminoethyl)-1,2,3,4-tetrahydroisoquinoline | maleate C₂₁H₂₅N₅O₆ | 443.450 | 200 | 54 | 56.87 | 5.68 | 15.79 | 56.48 | 5.48 | 15.74 |
| 77.1017 | " | " | aziridine | C₈H₁₀N₄O₂ | 194.192 | 218 | 52 | 49.48 | 5.19 | 28,85 | 49.40 | 5.15 | 28.71 |

TABLE C-continued $$(I)$$

| | R₁ | R₂/R₃ (CON group) | Formula | MW | mp | %C calc | %H calc | %N calc | %C found | %H found | %N found |
|---|---|---|---|---|---|---|---|---|---|---|---|
| 77.0508 | OC₂H₅ | -N(Et)CH₂CH₂NH- | C₁₃H₂₃N₅O₂ | 281.354 | 192 | 32 | 55.49 | 8.24 | 24.89 | 55.52 | 8.23 | 25.18 |
| 77.0540 | NH₂ | pyrrolidinyl-CH₂NH- | C₁₄H₂₃N₅O₂ | 293.364 | 193 | 30 | 57.31 | 7.90 | 23.87 | 57.19 | 7.62 | 23.90 |
| 77.0621 | OC₂H₅ | pyrrolidinyl-CH₂NH- | C₁₅H₂₅N₅O₂ | 307.390 | 162 | 50 | 58.61 | 8.20 | 22.79 | 58.52 | 8.26 | 22.95 |
| 77.0871 | O-n-C₃H₇ | pyrrolidinyl-CH₂NH- | C₁₅H₂₅N₅O₂ | 307.390 | 197 | 30 | 58.61 | 8.20 | 22.79 | 58.92 | 8.47 | 23.09 |
| 77.0872 | O-iso-C₃H₇ | 1-benzyl-4-piperidyl-NH | C₂₀H₂₇N₅O₂ | 369.456 | 157 | 25 | 65.01 | 7.37 | 18.96 | 64.85 | 7.20 | 19.15 |
| 77.1011 | N(CH₃)₂ | 1-benzyl-4-piperidyl-NH · HCl | C₂₀H₂₇N₅O₂·HCl | 405.921 | 227 | 50 | 59.17 | 6.95 | 17.25 | 58.87 | 7.21 | 17.56 |
| 77.1075 | OCH₃ | -N(Et)CH₂CH₂NH- oxalate | C₁₆H₂₇N₅O₆ | 385.416 | 142 | 72 | 49.86 | 7.06 | 18.17 | 49.77 | 7.26 | 18.47 |
| 77.1057 | " | pyrrolidinyl-CH₂NH- | C₁₅H₂₅N₅O₂ | 307.390 | 78 | 44 | 58.61 | 8.20 | 22.79 | 58.88 | 8.46 | 22.66 |

The derivatives of formula (I) were studied on laboratory animals and showed neuroleptic properties.

These properties were revealed in mice particularly by the test of antagonism to apomorphine straightening, effected according to the method described by G. Gouret and alia in S. Pharmcol. (Paris) 1973, 4, 341.

The 50 efficient doses obtained by intraperitoneal administration according to the above-mentioned test, the derivatives of formula (I) and Sulpiride chosen as reference compound, are shown in the following table D.

The acute toxicity was studied in mice intraperitoneally and the lethal doses estimated according to the method described by Miller and Tainter in Proc. Soc. Exper. Biol. Med. 1944, 57, 261, are shown in table D below.

TABLE D

| Tested compounds | Acute toxicity (mice) LD 50 mg/kg/ip | Apomorphine straightening ED 50 mg/kg/ip |
|---|---|---|
| SULPIRIDE | 170 | 37 |
| 76.0745 | 650 | 30 |
| 76.0843 | 300 | 6 |
| 76.0994 | 150 | 3 |
| 77.0208 | 500 | 3.5 |
| 77.0512 | 400 | 10 |
| 77.0489 | 330 | 3 |
| 77.0958 | 150 | 1.5 |
| 77.0862 | 300 | 30 |
| 77.0880 | 180 | 9 |
| 77.1006 | 175 | 3 |
| 77.1012 | 110 | 7 |
| 77.1017 | 300 | 15 |
| 77.1047 | 130 | 4.5 |
| 77.0766 | 300 | 12 |
| 77.0805 | 200 | 7 |
| 77.0878 | 150 | 10 |
| 77.0807 | 300 | 18.5 |
| 77.0886 | 125 | 17.5 |
| 77.0806 | 150 | 30 |
| 77.0840 | 95 | 10 |
| 77.1011 | 25 | 2.7 |
| 77.1075 | 200 | 16 |
| 77.1057 | 130 | 1.3 |
| 77.1243 | 150 | 15 |
| 77.1244 | 180 | 10 |
| 77.0508 | 300 | 30 |
| 77.0540 | 150 | 3 |
| 77.0621 | 150 | 15 |
| 77.0871 | 170 | 30 |
| 77.0872 | 115 | 11 |
| 77.0580 | 400 | 30 |
| 771120 | 180 | 3.4 |
| 771226 | 110 | 1.4 |
| 771261 | 70 | 2.4 |
| 771274 | 100 (0%) | 1.40 |
| 780079 | 225 | 11 |
| 780204 | 400 (30%) | 50 |
| 780326 | 130 | 5.8 |
| 780327 | 170 | 7 |
| 780336 | 170 | 1.80 |
| 780432 | 170 | 7.5 |
| 780457 | 160 | 17 |
| 780458 | 140 | 13 |
| 780505 | 155 | 15 |
| 780521 | 140 | 5.25 |
| 780522 | 130 | 10 |
| 780552 | 140 | 12.5 |
| 780560 | 100 | 3 |
| 780561 | 170 | 3.3 |
| 780656 | 140 | 6 |
| 780648 | 200 | 3.20 |
| 780680 | 275 | 7.20 |
| 780686 | 115 | 10 |
| 780700 | 200 | 17 |
| 780784 | 280 | 5.5 |
| 780836 | 140 | 9 |
| 780866 | 120 | 4.7 |
| 780886 | 140 | 10 |

TABLE D-continued

| Tested compounds | Acute toxicity (mice) LD 50 mg/kg/ip | Apomorphine straightening ED 50 mg/kg/ip |
|---|---|---|
| 780887 | 140 | 1 |
| 780905 | 175 | 0.88 |
| 780907 | 120 | 10 |
| 781017 | 150 | 4.10 |
| 781021 | 115 | 10.5 |
| 781022 | 140 | 3 |
| 781170 | 120 | 2.3 |
| 781171 | 100 | 3 |

As is shown by the results given in this table, the difference between efficient doses and 50 lethal doses is sufficient for derivatives of formula (I) to be used therapeutically.

These latter are suitable for treating troubles of the psychism i.e., as psychotropic drugs. they will be administered orally in the form of tablets, pills or capsules containing 100 to 300 mg active ingredient (6 to 8 per day), in the form of a solution containing 0.1 to 1% of active ingredient (20 to 60 drops, 1 to 3 times per day), parenterally in the form of injectable ampoules containing 10 to 100 mg active ingredient (6 to 8 ampoules per day).

What is claimed is:

1. Compounds of formula:

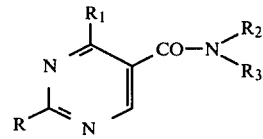 (I)

in which the group

represents:
the aziridine group:

, in which case the couple (R, R$_1$) assumes the value (NH$_2$, OCH$_3$);
the chain:

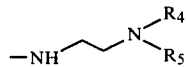

in which the group

represents:
the tetrahydro 1,2,3,4-isoquinoline-group, in which case the couple (R, R$_1$) assumes the value (NH$_2$, OCH$_3$);
a diethylamino group, in which case the couple (R, R$_1$) assumes anyone of the following values: (NH$_2$, OCH$_3$), (NH$_2$, OEt), (CH$_3$, OCH$_3$), (CH$_3$S, OCH$_3$),

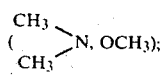

an anilino group, in which case the couple (R, R$_1$) assumes the value (NH$_2$, OCH$_3$);

a benzylamino group

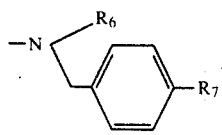

in which the couple (R$_6$, R$_7$)
assumes the value (CH$_3$, H), in which case the couple (R, R$_1$) assumes the value (NH$_2$, OCH$_3$);
assumes the value (Et, H), in which case the couple (R, R$_1$) assumes anyone of the following values (NH$_2$, OCH$_3$), (CH$_3$, OCH$_3$), (CH$_3$, OEt); or
assumes the value (Et, F), in which case the couple (R, R$_1$) assumes the value (CH$_3$, OCH$_3$) or (CH$_3$, OEt);

an N-ethyl N-cyclohexylmethyl amino group of formula

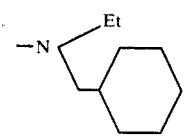

in which case the couple (R, R$_1$) assumes the value (CH$_3$, OCH$_3$); or an aryl-4 piperazino group of the formula:

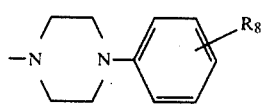

in which R$_8$ represents:
either a hydrogen atom or a fluorine atom in the para position, in which cases the couple (R, R$_1$) assumes the value (CH$_3$, OCH$_3$),
or a methoxy group in the ortho position, in which case the couple (R, R$_1$) assumes the values (NH$_2$, OCH$_3$) and (CH$_3$, OCH$_3$):

the chain

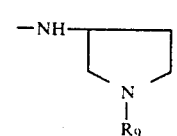

in which R$_9$ represents:
a cyclohexyl group, in which case the couple (R, R$_1$) assumes the value (NH$_2$, OCH$_3$): or
a benzyl or para fluorobenzyl group, in which cases the couple (R, R$_1$) assumes the values (NH$_2$, OCH$_3$) and (CH$_3$, OCH$_3$);
the chain

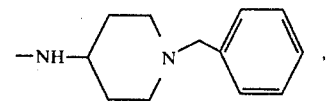

in which case the couple (R, R$_1$) assumes anyone of the following values: (NH$_2$, OCH$_3$), (CH$_3$, OCH$_3$), (H, OCH$_3$), (CH$_3$O, OCH$_3$),

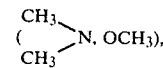

(CH$_3$NH, OCH$_3$), (NH$_2$, OC$_3$H$_{7iso}$);
the chain

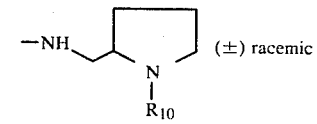

in which R$_{10}$ represents:
a methyl group, in which case the couple (R, R$_1$) assumes anyone of the following values: (NH$_2$, OCH$_3$), (CH$_3$, OCH$_3$), (CH$_3$, OEt), (Et, OEt);
an ethyl group, in which case the couple (R, R$_1$) assumes anyone of the following values: (NH$_2$, OCH$_3$), (NH$_2$, OEt), (NH$_2$, OC$_3$H$_{7n}$), (NH$_2$, OC$_3$H$_{7iso}$), (CH$_3$-NH, OCH$_3$),

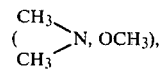

(H, OCH$_3$), (CH$_3$, OCH$_3$), (CH$_3$, OEt), (CH$_3$, OC$_3$H$_{7n}$), (CH$_3$, OC$_3$H$_{7iso}$), (Et, OEt), (C$_3$H$_{7n}$, OCH$_3$) (C$_3$H$_{7iso}$, OCH$_3$), (CH$_3$O, OCH$_3$), (CH$_3$S, OCH$_3$);
an n-propyl, n-butyl, benzyl or para-fluorobenzyl group, in which cases the couple (R, R$_1$) assumes the values: (NH$_2$, OCH$_3$) and (CH$_3$, OCH$_3$); or
a cylohexylmethyl or allyl group, in which cases the couple (R, R$_1$) assumes the value (CH$_3$, OCH$_3$);
the chain

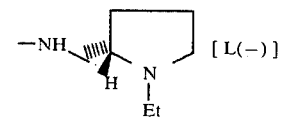

in which case the couple (R, R$_1$) assumes anyone of the following values: (CH$_3$, OCH$_3$), (CH$_3$, OEt),

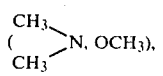

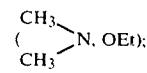

or
the chain

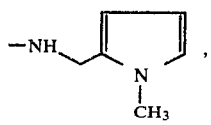

in which case the couple (R, $R_1$) assumes the value ($CH_3$, $OCH_3$).

2. A compound as claimed in claim 1 having the formula

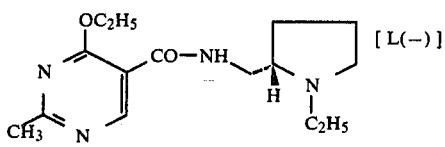

and the pharmacologically acceptable salts thereof.

3. A compound as claimed in claim 1 having the formula

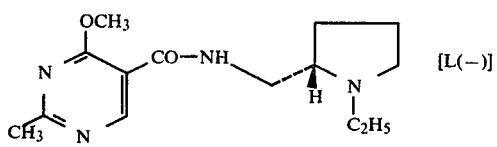

and the pharmacologically acceptable salts thereof.

4. A compound as claimed in claim 1, having the formula

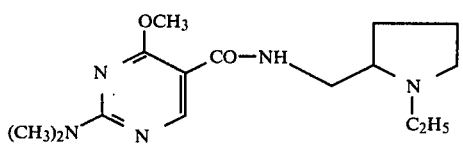

and the pharmacologically acceptable salts thereof.

5. A compound as claimed in claim 1 having the formula

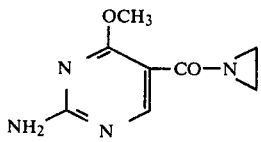

and the pharmacologically acceptable salts thereof.

6. A compound as claimed in claim 1 having the formula

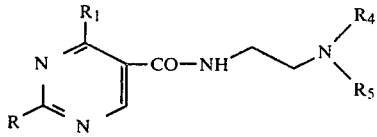

wherein

is selected from the group consisting of 1,2,3,4-tetrahydroisoquinoline, diethylamino, anilino,

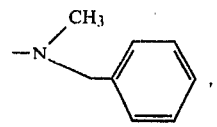

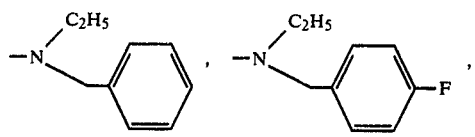

N-ethyl-N-cyclohexylmethylamino,

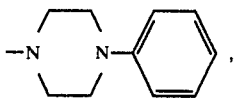

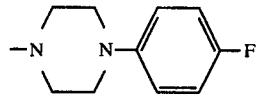

and 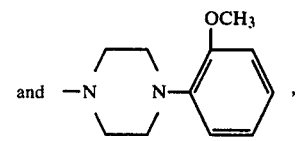

and wherein (a) when

is 1,2,3,4-tetrahydroisoquinoline, R is $NH_2$ and $R_1$ is $OCH_3$; (b) when

is diethylamino, then the pair R and $R_1$ is selected from the group consisting of (1) $NH_2$ and $OCH_3$, (2) $NH_2$ and $OC_2H_5$, (3) $CH_3$ and $OCH_3$, (4) $CH_3S$ and $OCH_3$, and (5)

and $OCH_3$; (c) when

is anilino, R is $NH_2$ and $R_1$ is $OCH_3$; (d) when is 

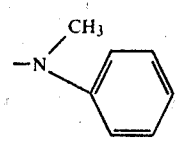

then R is $NH_2$ and $R_1$ is $OCH_3$; (e) when

is

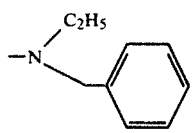

then the pair R and $R_1$ is selected from the group consisting of (1) $NH_2$ and $OCH_3$, (2) $CH_3$ and $OCH_3$, and (3) $CH_3$ and $OC_2H_5$; (f) when

is

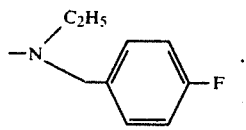

then the pair R and $R_1$ is selected from the group consisting of (1) $CH_3$ and $OCH_3$, and (2) $CH_3$ and $OC_2H_5$; (g) when

is N-ethyl-N-cyclohexylmethylamino, R is $CH_3$ and $R_1$ is $OCH_3$; (h) when

is

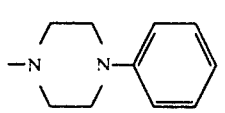

R is $CH_3$ and $R_1$ is $OCH_3$; when

is

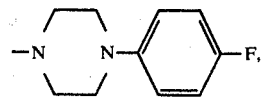

R is $CH_3$ and $R_1$ is $OCH_3$; and (j) when

is

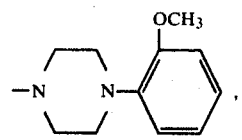

then the pair R and $R_1$ is selected from the group consisting of (1) $NH_2$ and $OCH_3$, and (2) $CH_3$ and $OCH_3$, and the pharmacologically acceptable salts thereof.

7. A compound as claimed in claim 1 having the formula

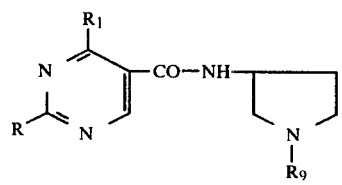

in which $R_9$ is cyclohexyl, benzyl or p-fluorobenzyl, and when $R_9$ is cyclohexyl R is $NH_2$ and $R_1$ is $OCH_3$, and when $R_9$ is benzyl or p-fluorobenzyl, the pair R and $R_1$ is selected from the group consisting of (1) $NH_2$ and $OCH_3$, and (2) $CH_3$ and $OCH_3$, and the pharmacologically acceptable salts thereof.

8. A compound as claimed in claim 1 having the formula

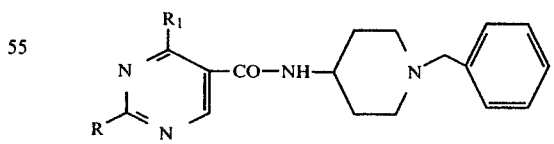

wherein the pair R and $R_1$ is selected from the group consisting of (1) $NH_2$ and $OCH_3$, (2) $CH_3$ and $OCH_3$, (3) H and $OCH_3$, (4) $OCH_3$ and $OCH_3$, (5) $N(CH_3)_2$ and $OCH_3$, (6) $NHCH_3$ and $OCH_3$, and (7) $NH_2$ and $OC_3H_7$(iso), and the pharmacologically acceptable salt thereof.

9. A compound as claimed in claim 1 having the formula

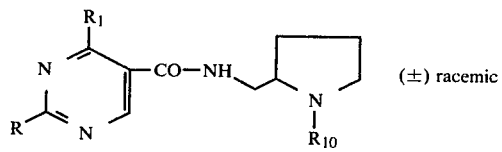 (±) racemic in which $R_{10}$ is selected from the group consisting of methyl, ethyl, n-propyl, n-butyl, benzyl, p-fluorobenzyl, cyclohexylmethyl and allyl, wherein (a) when $R_{10}$ is methyl, the pair R and $R_1$ is selected from the group consisting of (1) $NH_2$ and $OCH_3$, (2) $CH_3$ and $OCH_3$, (3) $CH_3$ and $OC_2H_5$, and (4) $C_2H_5$ and $OC_2H_5$, (6) when $R_{10}$ is ethyl, the pair R and $R_1$ is selected from the group consisting of (1) $NH_2$ and $OCH_3$, (2) $NH_2$ and $OC_2H_5$, (3) $NH_2$ and $OC_3H_7(n)$, (4) $NH_2$ and $OC_3H_7(iso)$, (5) $NHCH_3$ and $OCH_3$, (6) $N(CH_3)_2$ and $OCH_3$, (7) H and $OCH_3$, (8) $CH_3$ and $OCH_3$, (9) $CH_3$ and $OC_2H_5$, (10) $CH_3$ and $OC_3H_7(n)$, (11) $CH_3$ and $OC_3H_7(iso)$, (12) $C_2H_5$ and $OC_2H_5$, (13) $C_3H_7(n)$ and $OCH_3$, (14) $C_3H_7(iso)$ and $OCH_3$, (15) $OCH_3$ and $OCH_3$, and (16) $CH_3S$ and $OCH_3$, (c) when $R_{10}$ is n-propyl, n-butyl or p-fluorobenzyl, the pair R and $R_1$ is selected from the group consisting of (1) $NH_2$ and $OCH_3$, and (2) $CH_3$ and $OCH_3$, and (d) when $R_{10}$ is cyclohexylmethyl or allyl, then R is $CH_3$ and $R_1$ is $OCH_3$, and the pharmacologically acceptable salts thereof.

10. A compound as claimed in claim 1 having the formula

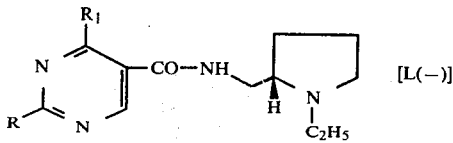 [L(−)]

wherein the pair R and $R_1$ is selected from the group consisting of (1) $CH_3$ and $OCH_3$, (2) $CH_3$ and $OC_2H_5$, (3) $N(CH_3)_2$ and $OCH_3$, and (4) $N(CH_3)_2$ and $OC_2H_5$, and the pharmacologically acceptable salts thereof.

11. A compound as claimed in claim 1 having the formula

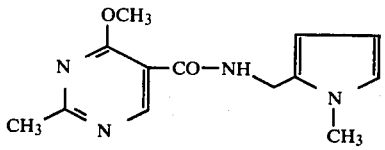

and the pharmacologically acceptable salts thereof.

12. A medicinal composition comprising a therapeutically effective amount of a compound as claimed in claim 1 in combination with a pharmacologically acceptable carrier.

* * * * *